US00PP15158P2

(12) United States Plant Patent
Olesen et al.

(10) Patent No.: US PP15,158 P2
(45) Date of Patent: Sep. 21, 2004

(54) ROSE PLANT NAMED 'POULEN008'

(50) Latin Name: *Rosa hybrida*
Varietal Denomination: POULen008

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 4 days.

(21) Appl. No.: 10/738,158

(22) Filed: Dec. 16, 2003

(51) Int. Cl.[7] ..... A01H 5/00
(52) U.S. Cl. ..... Plt./137
(58) Field of Search ..... Plt./137, 136

*Primary Examiner*—Anne Marie Grunberg
*Assistant Examiner*—June Hwu

(57) ABSTRACT

A new garden rose plant of the hybrid tea class which has abundant, pink flowers and attractive foliage. This new and distinct variety has shown to be uniform and stable in the resulting generations from asexual propagation.

2 Drawing Sheets

Bontanical classification: *Rosa hybrida*.
Variety denomination: 'POULen008'.

SUMMARY OF THE INVENTION

The present invention constitutes a new and distinct variety of garden rose plant which originated from a controlled crossing between an female parent, an unnamed seedling, and a male parent plant named 'POULsyng', described and illustrated in U.S. Plant Pat. application Ser. No. 09/268,299 dated Mar. 16, 1999, now abandoned. The two parents were crossed during the summer of 1995 and the resulting seeds were planted in a controlled environment in Fredensborg, Denmark. The new variety is named 'POULen008'.

The new variety may be distinguished from its unnamed female seed parent by the following combination of characteristics:

1. While the seed parent has white flowers, the same of 'POULen008' are pink.
2. While the seed parent has semi-double blooms, the same of 'POULen008' are double.
3. While the seed parent has little or no scent, 'POULen008' has a strong floral scent.

The new variety may be distinguished from its male pollen parent, 'POULsyng' by the following combination of characteristics:

1. While the pollen parent 'POULsyng' has peached color blooms the same of 'POULen008' are pink.
2. As sepals unfold the flower bud color of the male parent is Yellow-Green Group 150D. Bud color of 'POULen008' is Orange-White Group 159A.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Disease resistance;
4. Exceptional rose fragrance.

This combination of qualities is not present in previously available commercial cultivars of this type, known to the inventors, and distinguish 'POULen008' from all other varieties of which we are aware.

As part of their rose development program, L. Pernille Olesen and Mogens N. Olesen germinated the seeds from the aforementioned hybridization during winter of 1995 and conducted evaluations on the resulting seedlings in a controlled environment in Fredensborg, Denmark.

'POULen008' was selected in the spring 1996 by the inventors as a single plant from the progeny of the aforementioned hybridization.

Asexual reproduction of 'POULen008' by traditional budding and rooted cuttings was first done by L. Pernille and Mogens N. Olesen in their nursery in Fredensborg, Denmark in July, 1996. This initial and other subsequent asexual propagations conducted in controlled environments have demonstrated that the characteristics of 'POULen008' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULen008'. Specifically illustrated in SHEET 1:

FIG. 1.1; Open flower, stem showing open flower, branching, and the attachment of leaves;

FIG. 1.2; Flower bud closed, and partially open;

FIG. 1.3; Flower petals, detached;

Specifically illustrated in SHEET 2:

FIG. 2.1; Sepals, receptacle, and peduncle;

FIG. 2.2; Mature leaves;

FIG. 2.3; Bare stems exhibiting thorns.

DETAILED DESCRIPTION OF THE VARIETY

The following is a description of 'POULen008', as observed in its growth in a field nursery in Jackson County, Oreg. Observed plants are 3 years of age, grown on *Rosa multiflora* understock. Color references are made using The Royal Horticultural Society (London, England) Colour Chart, 1995, except where common terms of color are used.

For a comparison, several physical characteristics of the rose variety 'POULheart', a rose variety from the same inventors described and illustrated in U.S. Plant patent application Ser. No. 09/270,179 dated Mar. 15, 1999, now abandoned, are compared to 'POULen008' in Chart 1.

CHART 1

| | 'POULen008' | 'POULheart' |
|---|---|---|
| General Tonality | Orange Group 29D. | Yellow-White Group 158B. |
| Basal petal spot on outermost petals. | Outer side Yellow Group 11B, inner side Yellow Group 9C. | Outer side Green-Yellow Group 1D, inner side Yellow Group 3B. |
| Size of compound leaf | 150 mm (l) × 110 mm (w). | 100 (l) × 90 (w). |

Parents:

*Female Seed Parent.*—Unnamed plant.

*Male Pollen Parent.*—'POULsyng'.

FLOWER AND FLOWER BUD

Blooming habit: Recurrent.

Flower bud:

*Size.*—Upon opening, 40 mm in length from base of receptacle to end of bud.

*Bud form:*—Ovoid.

*Bud color.*—As sepals unfold, petals are Orange-White Group 159A with intonations of Red Group 49C.

*Sepals.*—Upper surface: Color: Yellow-Green Group 144B. Texture: Somewhat rough. Strongly to moderately pubescent. Lower Surface: Color: Yellow-Green Group 144A with anthocyanic intonations of Greyed-Red Group 181A. Texture: Smooth with sparse stipitate glands. Sepal Shape: Sepal apex is cirrhose. Base is flat at union with receptacle. Sepal Margin: Margins have weak foliaceous appendages on three of the five sepals. Size: 35 mm (l)×13 mm (w).

*Receptacle.*—Surface: Smooth. Shape: Broadly urn-shaped. Size: 8 mm (h)×12 mm (w). Color: Yellow-Green Group 144A.

*Peduncle.*—Surface: Smooth. Very few stipitate glands. Length: 55 to 60 mm. Color: Yellow-Green Group 144A with light intonations of Greyed-Red Group 181A. Strength: Strong.

*Borne:*—Singularly.

Flower bloom:

*Fragrance.*—Strong floral scent.

*Duration.*—The blooms have a duration on the plant of approximately 10 days.

*Size.*—Flower diameter is 90 to 100 mm when open.

*Form.*—General shape is a deep cup with moderately reflexed petals overlapping.

Shape of flower when viewed from the side:

Upon opening, upper part: Flat.

Upon opening, lower part: Flat.

Open flower, upper part: Flat.

Open flower, lower part: Concave.

Petalage: 65 petals under normal conditions with 15 petaloids.

Color:

Upon opening, petals:

*Outermost petals.*—Outer side: Orange Group 27C from marginal to middle zone. Basal to middle zone Yellow-White Group 158A. Inner Side: Orange Group 27C from marginal to middle zone. Basal to middle zone Yellow-White Group 158A.

*Innermost petals.*—Outer side: Orange Group 27A from marginal to middle zone with intonations of Red Group 38C at petal margin. Basal zone coloration is Yellow-White Group 158B. Inner Side: Yellow-White Group 158B at middle and basal zones. Orange Group 27A at marginal to middle zones.

Upon opening, basal petal spots:

*Outermost petals.*—Outer side: None observed. Inner side: Yellow Group 7B, petal spots are very small.

*Innermost petals.*—Outer side: Yellow Group 7D. Inner Side: Yellow Group 7B.

After opening, petals:

*Outermost petals.*—Outer side: Red-Purple Group 62C at marginal zone, gradually blending to become Yellow Group 11D at middle zone. Inner Side: Red-Purple Group 62C at marginal zone, gradually blending to become Yellow Group 11D at middle zone.

*Innermost petals.*—Outer side: Red-Purple Group 62C at marginal zone, gradually blending to become Yellow Group 11D at middle zone. Inner Side: Red-Purple Group 62C at marginal zone, gradually blending to become Yellow Group 11D at middle zone.

After opening, basal petal spots:

*Outermost petals.*—Outer Side: Yellow Group 11B. Inner Side: Yellow Group 9C.

*Innermost petals.*—Outer Side: Yellow Group 11B Inner Side: Yellow Group 9C.

General tonality: On open flower Orange Group 29D. No change in the general tonality at the end of the 7th day. Afterwards, general tonality is Orange Group 29D.

Petals

*Petal Reflex*—Petals reflex slightly.

*Margin.*—Entire and uniform with weak undulations of margin.

*Shape.*—Apex: Round. Base: Acute.

*Size:*—50 mm (l)×50 mm (w).

*Texture.*—Smooth.

*Thickness.*—Average to thin.

*Arrangement.*—Not Formal.

Petaloids:

*Quantity.*—10 to 15.

*Color.*—Upper Surface: Red Group 38C. Lower Surface: Red Group 50D.

*Size.*—35 to 45 mm (l)×15 to 20 mm (w).

Reproductive organs:

*Pistils.*—Length: 8 mm long. Quantity: 95.

*Pollen.*—Color: Yellow-Orange Group 14B Quantity: Average.

*Anthers.*—Size: 2 mm long. Color: Yellow-Orange Group 14D. Quantity: 147 (actual count).

*Filaments.*—Color: Yellow Group 10A. Length: 11 mm.

*Stigmas.*—Inferior in locations to height of the filaments and anthers. Color: Yellow-White Group 158B.

*Styles.*—Color: Yellow-White Group 158B

*Hips.*—None Observed in the field nursery in Jackson County Oreg.

PLANT

Plant growth: Moderate, upright to bushy. When grown as a budded field grown plant on *Rose multiflora* understock, the average height of the plant is 100 to 150 cm. Average width is 100 cm.

Stems:

*Color.*—Young wood: Yellow-Green Group 144A. Older wood: Yellow-Green Group 144A.

*Surface Texture.*—Young wood: Smooth. Older wood: Smooth.

Thorns:

*Incidence.*—5 thorns per 10 cm of stem.

*Length.*—7 mm.

*Color.*—Greyed-Orange Group 174A.

*Shape.*—Deeply concave to concave.

Plant foliage: Normal number of leaflets on leaves in middle of the stem: 5 leaflets.

*Compound Leaf size.*—150 mm (l)×110 mm (w).

*Color.*—Mature Foliage: Upper Leaf Surface: Yellow-Green Group 146A to 146B. Lower Leaf Surface: Yellow-Green Group 147C. Juvenile foliage: Upper Leaf Surface: Yellow-Green Group 146A to 146B. Lower Leaf Surface: Yellow-Green Group 147C.

Plant leaves and leaflets:

*Stipules.*—Size: 20 mm to 25 mm in length. Color: Yellow-Green Group 144A. Margins: Stipitate glands are scant to average. Anthocyanin: Very weak. Color: Greyed-Red Group 181A.

*Petiole.*—Length: 40 mm to 50 mm. Color: Yellow-Green Group 144B with weak intonations of Greyed-Red Group 181A. Anthocyanin: None observed. Underneath: Prickles of 2 mm in length.

*Rachis.*—Size: 40 mm to 50 mm in length. Color: Yellow-Green Group 144B with weak intonations of Greyed-Red Group 181A. Anthocyanin: None observed. Underneath: Prickles of 2 mm in length.

*Leaflet.*—size: 60 to 65 mm (l)×44 to 45 mm (w). Edge: Serrated. Shape: Generally orbicular. Apex: Cuspidate. Base: Rounded. Texture: Smooth. Arrangement: Odd pinnate. Venation: Reticulate. Glossiness: Moderately glossy. Thickness: Thick.

Disease resistance: Above average resistance to mildew, rust, black spot, and Botrytis under normal growing conditions in Jackson County, Oreg.

Cold hardiness: The variety 'POULen008' has been found to be cold tolerant to USDA Cold Hardiness Zone 6.

We claim:

1. A new and distinct variety of rose plant of the hybrid tea rose class, substantially as herein illustrated and described as a distinct and novel rose variety due to its abundant pink, disease resistance, and extended period of bloom.

* * * * *

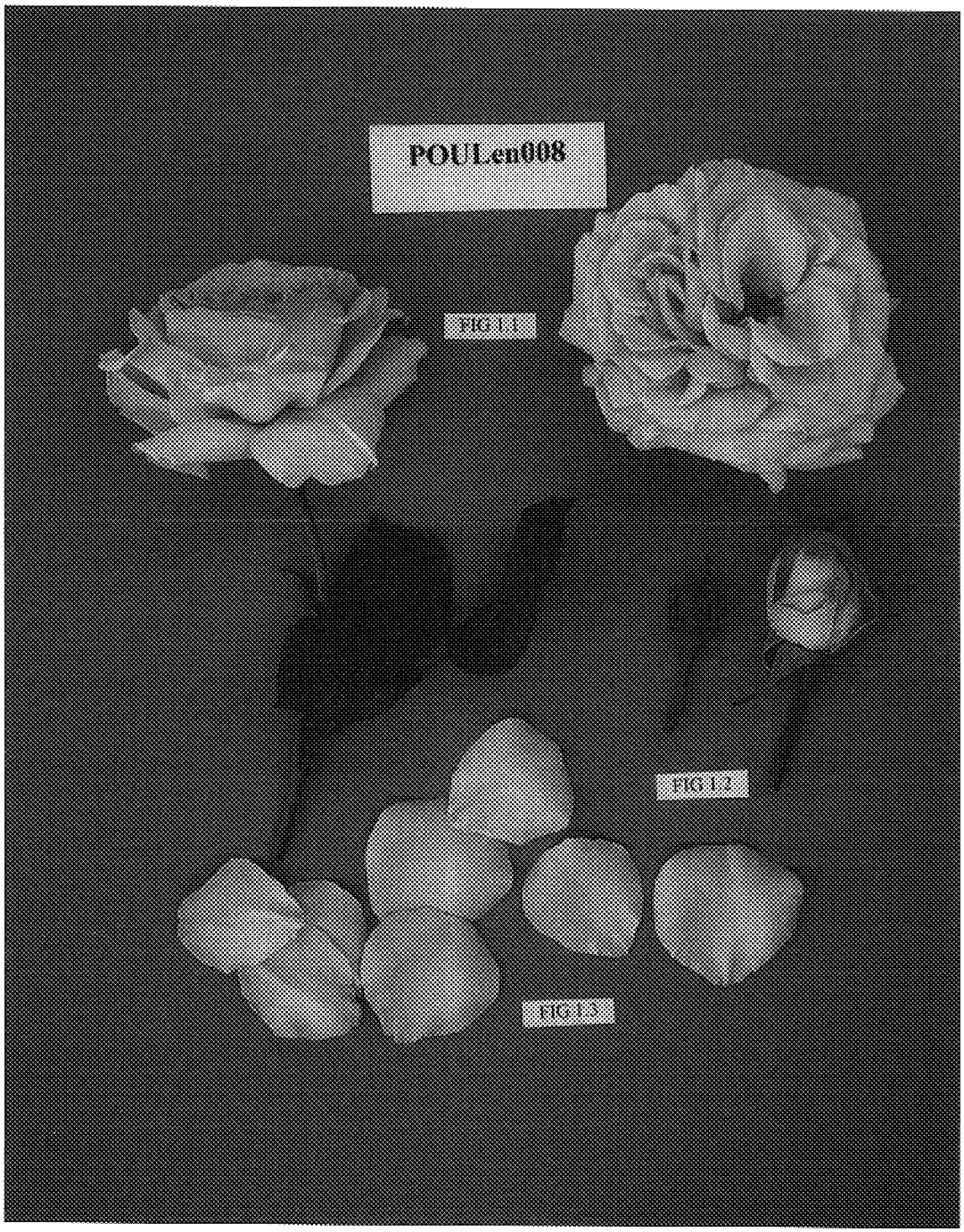
POULen008
FIG 1.1
FIG 1.2
FIG 1.3

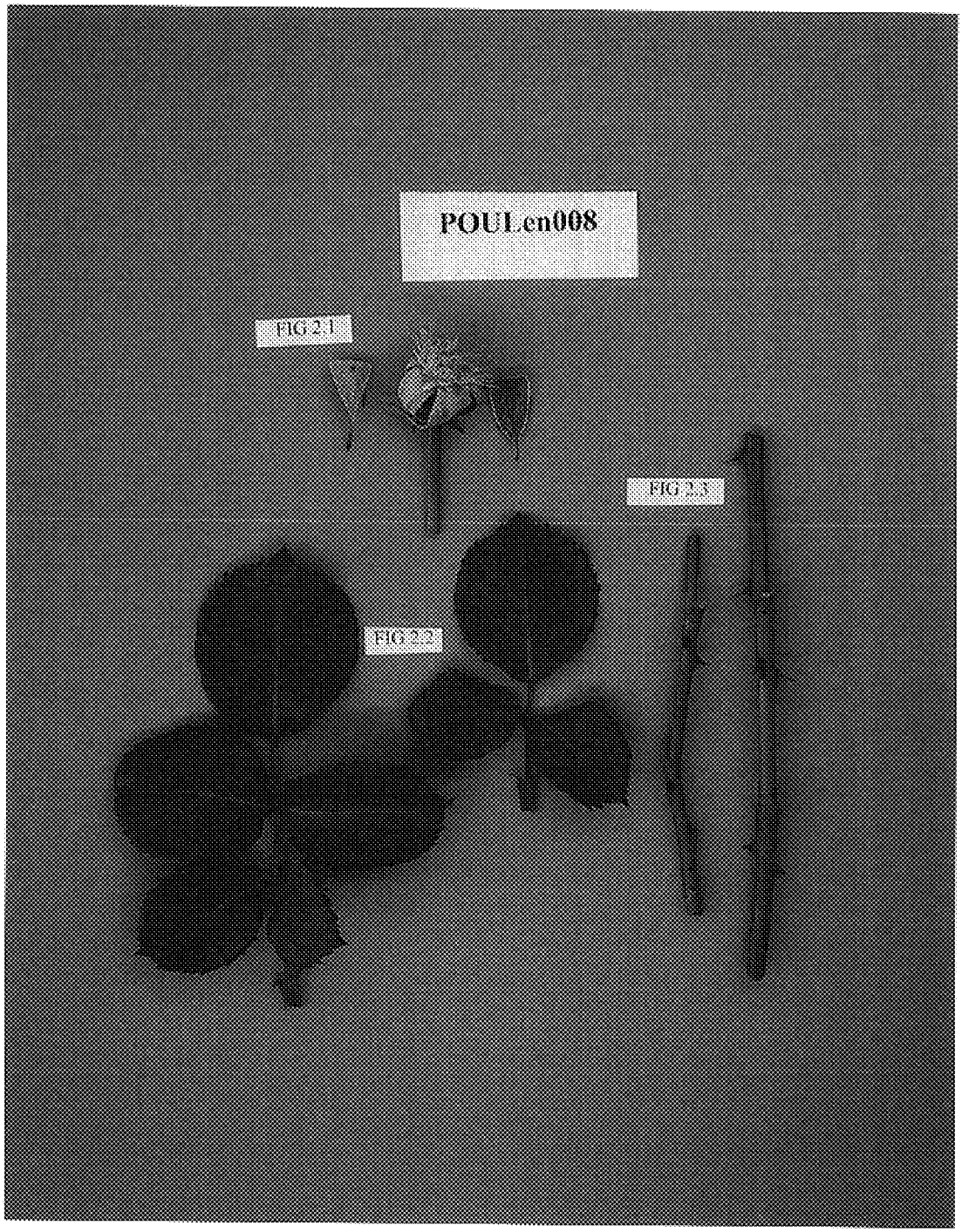
POULen008
FIG 2.1
FIG 2.2
FIG 2.3